(12) United States Patent
Haider

(10) Patent No.: US 7,706,587 B2
(45) Date of Patent: Apr. 27, 2010

(54) METHOD FOR CREATION OF AN OVERVIEW OF MEDICAL DATA SETS

(75) Inventor: Sultan Haider, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 978 days.

(21) Appl. No.: 11/473,772

(22) Filed: Jun. 23, 2006

(65) Prior Publication Data
US 2006/0291709 A1 Dec. 28, 2006

(30) Foreign Application Priority Data
Jun. 23, 2005 (DE) .................. 10 2005 029 241

(51) Int. Cl.
*G06K 9/00* (2006.01)
(52) U.S. Cl. .................. 382/128; 382/131; 382/132; 715/700
(58) Field of Classification Search .................. 382/100, 382/128–133, 173, 224, 305; 600/424, 410; 128/899; 378/5; 715/700, 727, 733, 762
See application file for complete search history.

(56) References Cited

U.S. PATENT DOCUMENTS

| | | | | |
|---|---|---|---|---|
| 4,160,906 A | * | 7/1979 | Daniels et al. | 378/97 |
| 6,813,512 B2 | * | 11/2004 | Aldefeld et al. | 600/410 |
| 7,450,747 B2 | * | 11/2008 | Jabri et al. | 382/132 |
| 2003/0015207 A1 | | 1/2003 | Herold et al. | |
| 2005/0085720 A1 | * | 4/2005 | Jascob et al. | 600/424 |
| 2005/0209888 A1 | * | 9/2005 | Oowaki et al. | 705/3 |

* cited by examiner

*Primary Examiner*—Samir A Ahmed
*Assistant Examiner*—Ali Bayat
(74) *Attorney, Agent, or Firm*—Schiff Hardin LLP

(57) ABSTRACT

In a method for creation of an overview of medical data sets, a plurality of medical data sets exist regarding a patient and the data sets are associated with categories, and an overview image of at least one part of the patient is generated by means of an imaging modality. A localization within the patient is associated with each of the data sets, and the overview image is shown on a display medium. Markings are generated and shown at points of the overview image that correspond to the localizations of the data sets. The categories that exist with regard to at least one of the points are likewise displayed.

13 Claims, 2 Drawing Sheets

METHOD FOR CREATION OF AN OVERVIEW OF MEDICAL DATA SETS

BACKGROUND OF THE INVENTION

1. Field of the Invention

The present invention concerns a method for creation of an overview representation of medical data sets.

2. Description of the Prior Art

In medical diagnostics, it is frequently necessary for a doctor or radiologist to evaluate a number of data sets in the generation of a finding. Using existing data sets originating, for example, from various imaging examination modalities (such as magnetic resonance tomography or computed tomography), it is the object of the doctor to establish which treatment course and which therapeutic measures are to be considered for the patient. Particularly in cancer therapy, the therapeutic measures depend on the current state of the cancer. It is thereby important to establish the localization of the tumors and possible metastases in order to be able to assess the extent, if any, to which further organs are affected or can be affected by the cancer. For example, by means of magnetic resonance whole-body examinations it is possible to map the entire body of a patient and possibly present metastases. However, since functional information from the magnetic resonance measurement does not always exist, the differentiation between benign and malignant tumors, is not always possible. Further examinations, for example by means of computed tomography or positron emission tomography, are therefore frequently necessary.

The medical assessment of the existing data sets of a patient frequently represent a problem for the treating doctor since these can be surveyed only with difficulty sue to the large abundance of data. It is thus difficult to keep track of the associations between multiple data sets, in particular when these have been acquired by means of different examination modalities. A frequent change between the observation of the data sets is additionally necessary, which further extends and complicates the process of making a finding.

SUMMARY OF THE INVENTION

An object of the present invention is to provide a method that allows medical data sets to be represented clearly and concisely.

This object is achieved in accordance with the present invention by a method wherein the data sets that are present are initially classified in categories, for example, already during the generation of the data sets. Alternatively, previously obtained data sets can also be classified in such categories. One of the categories is, for example, the modality used to the examination. Consequently, each data set is associated with the examination modality with which it was generated, for example magnetic resonance tomography, computer tomography or ultrasound.

An overview image of at least one part of a patient is generated by means of an imaging modality and a localization within the patient is associated with each of the data sets. Each then data set can be localized using the overview image. The overview image can be, for example, a magnetic resonance whole-body exposure. It is shown on a display medium together with the present categories. Moreover, markings are shown at points on the overview image that correspond to the localizations of the data sets within the patient. By the categorization of the data sets and the representation of the markings on the overview image, a direct overview of the data sets present regarding the respective patient results for the doctor. Using the overview image, the doctor can establish at a glance the points within the patient at which data sets exist. By the additional display of the existing categories, the doctor can easily review which examinations have already been implemented. It can thereby be more easily assessed which further therapy or examination course should be considered for the patient.

In an embodiment of the method, a coordinate system is generated and coordinates within the patient are automatically associated with the data sets. Through the definition of the coordinate system, in particular data sets within the overview image that have been acquired by means of various imaging examination modalities (for example magnetic resonance or computed tomography) can be exactly associated with a position within the patient.

In another embodiment of the method, an examination plan and/or a therapy plan for the patient is determined and displayed based on a medical problem (question). Using the proposed examination plan, the doctor can easily establish the further examination plan for the respective patient and can organize further action based thereon. At the beginning of the method, the doctor, for example, can select one problem from a list of predetermined problems, using which the method proceeds further. The list is thereby expandable and modifiable. The displayed examination workflow can include, for example, suggestions for further examinations for cancer diagnosis. It serves as a guideline for the doctor for further planning. Moreover, therapy possibilities are displayed regarding already-identified diseases. If a number of alternatives for an examination workflow are available for a problem, these are displayed. The doctor can then individually design an examination workflow according to his or her ideas. The possibility is always given to the doctor to arbitrarily modify the proposed examination workflow. A modified examination workflow is stored as a further alternative for the respective problem and displayed as well given the next display of examination workflows.

DESCRIPTION OF THE PREFERRED EMBODIMENTS

Figure 1:
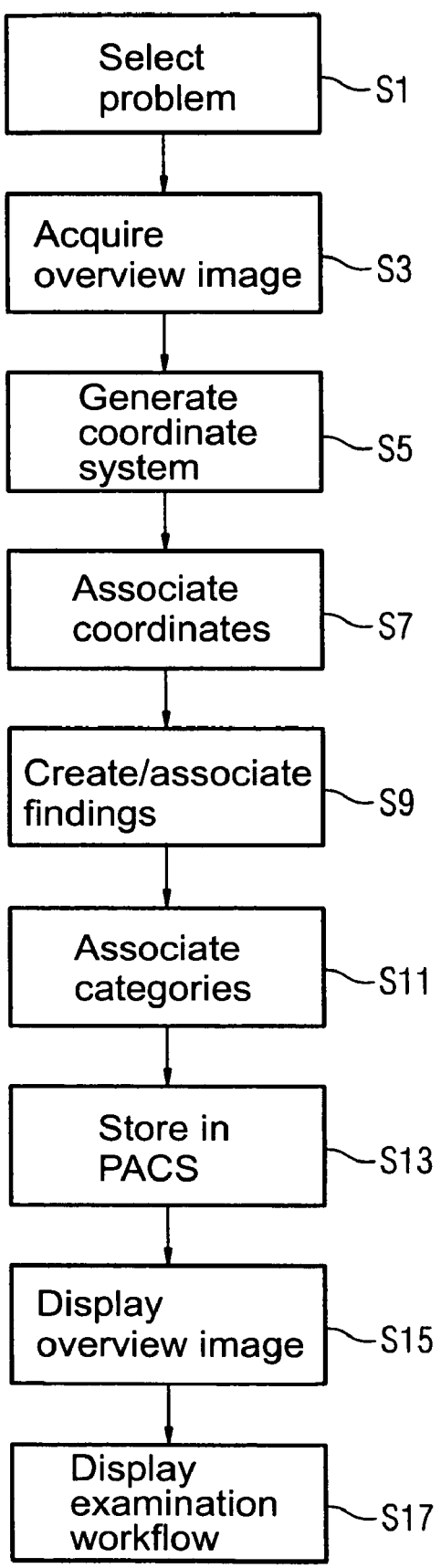
FIG. 1 is a schematic workflow diagram of an exemplary embodiment of the inventive method.

A schematic workflow diagram for a preferred embodiment of the method is shown in FIG. 1. In a first method step S1, a medical problem is selected from a list of existing problems. The problems are stored in a databank and, for example, include the question of whether a malignant tumor exists. In a second method step S3, an overview image of the patient is acquired by means of a whole-body magnetic resonance examination. In a third method step S5, the origin of a coordinate system is defined within the overview image. The origin can thereby be manually selected by the treating doctor on a representation of the overview image, or can be automatically established by means of pattern recognition using the specified problem. For example, given a whole-body representation the origin is thus automatically established on the uppermost bone of the lumbar spinal column, with the bone being automatically identified within the overview image.

In a fourth method step S7, data sets that exist with regard to the patient are associated with coordinates within the defined coordinate system, such that each data set can be distinctly localized within the patient. In a fifth method step S9, the data sets are provided with findings by the doctor or, in the event that already-assessed data sets exist, these are associated with the corresponding data sets. Alternatively, using the problem it is possible to be able to fined and indicate lesions in an automated manner by means of pattern recognition. Within magnetic resonance examinations, an automatic detection of metastases within the patient is possible by the analysis of contrast changes. In a sixth method step S11, the data sets are classified in suitable categories using the point in time of their generation and their type. For example, computed tomography, magnetic resonance tomography, ultrasound or positron emission tomography can be selected as the type (modality). Within the respective examination method, there are further categories dependent on the measurement method used. For example, within magnetic resonance tomography there are multiple imaging possibilities in order to examine the patient using the medical problem. Here T1-weighting and T2-weighting, which show various tissue types with different contrast, are examples. Corresponding categories are present and are assigned to the data sets.

For an operation in a hospital it is frequently necessary to make the data sets centrally accessible. Doctors within the hospital and/or at other locations have access to a central databank with the data sets. This databank can be fashioned, for example, as a PACS (Picture Archiving and Communication System). In a seventh method step S13, the data sets are stored within the PACS with their associated coordinates and the associated overview image.

In an eighth method step S15, the overview image is shown on a display medium. Markings that indicate those points of the patient at which data sets already exist are additionally displayed within the overview image. The categories for which data sets exist for the respective patient can be optionally displayed as well. The doctor thus receives, in a simple manner, an overview of the data sets that are present with regard to the patient and can create findings. In a ninth method step S17, using the existing data and the selected problem, an examination workflow is displayed that serves as a guideline for the doctor in the planning of the further procedure. In the case of an identified tumor, for example, further examinations are suggested in order to acquire detailed information about the tumor. These can be further magnetic resonance examinations, for example,. A detailed whole-body examination can likewise be proposed in order to examine the patient for metastases. Therapy measures for identified diseases can likewise be contained in the suggestion.

For each problem, the corresponding examination workflows are stored in the databank and are retrieved dependent on the findings and the problem. A number of alternatives for the examination workflow generally exist for each problem, which alternatives are shown. According to his or her ideas, from the displayed suggestions the doctor can assemble an examination and therapy plan that is optimal for the patient and add new steps or modify displayed steps as needed. The examination workflow so created is stored in the databank and is available given the next selection of the corresponding problem.

Figure 2:
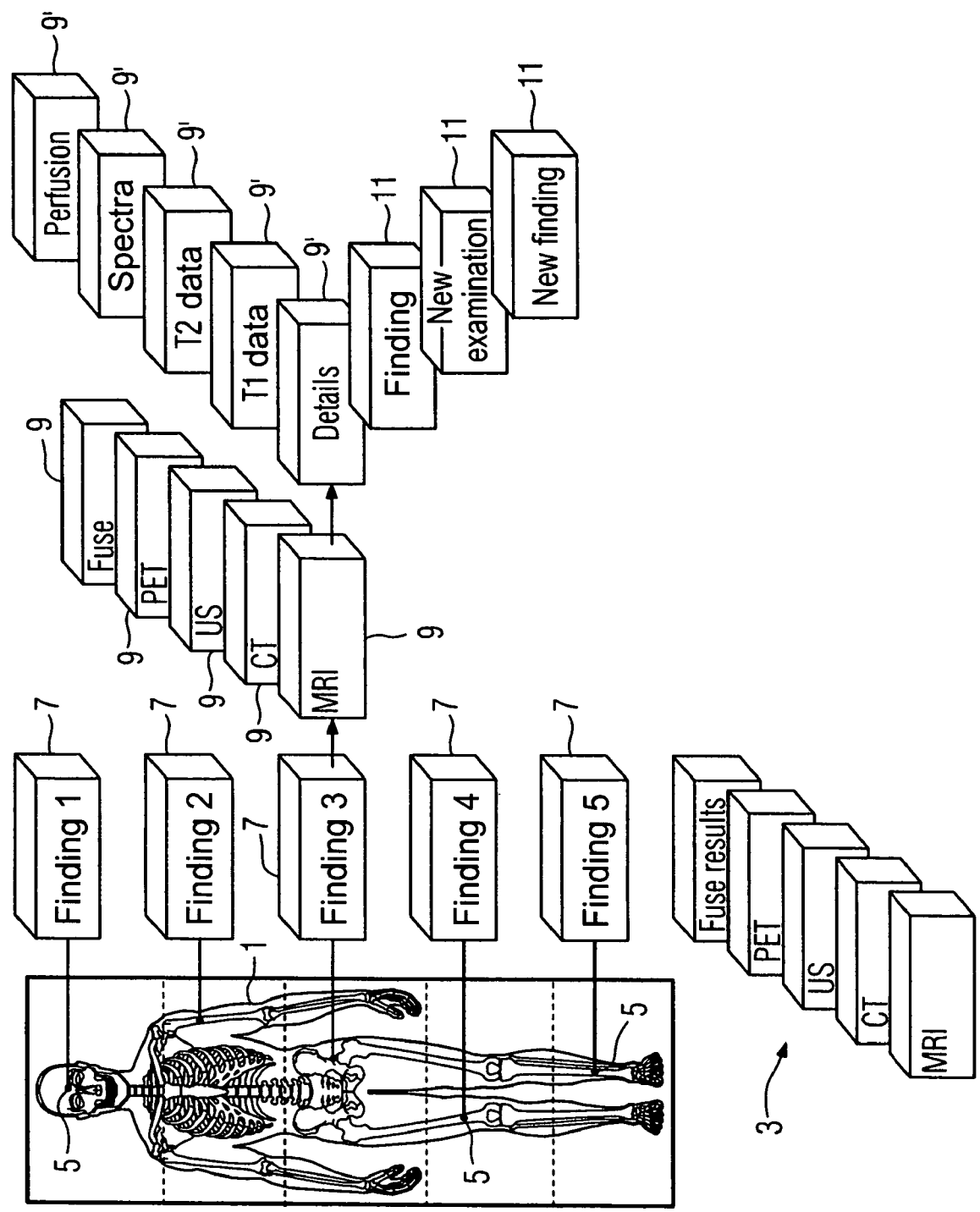
FIG. 2 schematically shows an overview image with markings and associated findings in accordance with the invention.

A whole-body exposure 1 of a patient is schematically shown as an overview image in FIG. 2. An overview 3 of categories in which data sets regarding to the patient exist is likewise shown. Alternatively, these can be masked. The points of the patient at which data sets exist are characterized by markings 5 in the overview image 1. Each of the markings 5 is connected with a comment field 7 on which, for example, a short finding is noted. The comment fields 7 can be operated with the computer mouse. By clicking on a comment field 7, the data sets associated with the corresponding point are loaded from the central databank of the PACS and shown on the display medium. In the event that multiple data sets exist with regard to a marking 5, the categories 9 associated with them are initially displayed so that the doctor receives an overview. The data set is loaded by clicking on the respective category 9. In the event that multiple data sets exist in a category 9 (which multiple data sets can be differentiated by further categories 9'), sub-categories of the data sets are shown in turn. Alternatively, multiple data sets can be displayed simultaneously. The doctor thus arrives at the desired data sets in a simple manner and can always maintain the overview.

Further buttons 11 are available to the doctor with which he or she can, for example, create a new finding by interaction with the computer mouse, or can cause an already-created finding to be displayed. A button 11 is likewise present via which a new examination or a therapy can be input into the PACS. An examination workflow is thereby automatically suggested.

It is additionally possible for the doctor to have a sequence of data sets displayed using criteria that he or she places within a category 9 or 9'. This is useful, for example, in order to be able to compare examinations that are temporally separated from one another. Two points in time before and after a chemotherapy could be established as a criterion, and only examinations by means of computed tomography could be established as a further criterion.

The described method ensures that only those data that a doctor wishes to view directly are transferred to his local terminal. It is consequently no longer necessary to transfer all data existing regarding the patient to each of the examining doctors, which distinctly reduces the data traffic within the network infrastructure. This is particularly true when some data must be assessed by a specialist who is not resident in the hospital at which the data was generated.

If further examinations are effected on the patient, for example by means of further imaging examination modalities, coordinates within the coordinate system of the overview image are also associated with these data sets. The data sets are correspondingly incorporated into the categories and are subsequently made available for medical assessment in the (updated) overview.

Moreover, standardized examination and therapy workflows for various clinical scenarios (disease patterns) exist in the central databank. These are shown on the display medium using the existing finding and data sets for the respective patient. They represent guideline for the doctor for planning further examinations or therapy of the patient. Multiple workflows for the various clinical scenarios can also be stored as alternatives and can be appropriately displayed.

An overview through which various doctors have access to a large number of data sets of a patient can be generated in a simple manner with the described method. Planning of a therapy or a further examination plan for the respective patient is thereby made easier.

Although modifications and changes may be suggested by those skilled in the art, it is the intention of the inventor to embody within the patent warranted hereon all changes and modifications as reasonably and properly come within the scope of his contribution to the art.

I claim as my invention:

1. A method for generating an overview of a plurality of medical data sets that exist with respect to a patient and that are respectively associated with categories, said method comprising the steps of:

generating an overview image of at least a portion of the patient with a medical imaging apparatus;

for each of said data sets, generating an electronic localization of the data set within the patient;

displaying the overview image at a display medium;

generating and displaying respective markings at respective points in said overview image at said display medium that correspond to the respective localizations of the data sets; and by electronic user interaction with the respective points via said display medium, automatically displaying all categories associated with the data set localized by that point in the overview image.

2. A method as claimed in claim 1 comprising classifying said data sets in said categories dependent on a point in time that each data set was generated and dependent on an examination modality used to generate the respective data set.

3. A method as claimed in claim 1 wherein at least some of said data sets are categorized in multiple categories.

4. A method as claimed in claim 1 wherein at least one of said categories comprises a plurality of sub-categories, and associating at least one of said sub-categories with each of said data sets within the category.

5. A method as claimed in claim 4 comprising, by user interaction via said display medium, allowing user selection of any of said sub-categories.

6. A method as claimed in claim 5 comprising, upon selection of one of said sub-categories, displaying at least one of said data sets at said display medium that is associated with the selected sub-category.

7. A method as claimed in claim 4 comprising displaying at least a portion of said categories and sub-categories in a tree structure at said display medium.

8. A method as claimed in claim 4 comprising displaying a plurality of said data sets in a sequence at said display medium, and establishing said sequence dependent on criteria associated with the categories and sub-categories with which said data sets are associated.

9. A method as claimed in claim 1 comprising storing said data sets at a central server, and transferring said data sets from said central server to said display medium via a communication link between said central server and a computer terminal associated with said display medium.

10. A method as claimed in claim 1 comprising, at said display medium, automatically displaying a coordinate system within the patient and automatically associating the respective data sets at said display medium with coordinates of said coordinate system that correspond to the respective localizations of the data sets.

11. A method as claimed in claim 10 comprising automatically establishing an origin of said coordinate system in the overview image of the patient.

12. A method as claimed in claim 1 comprising, via said display medium, displaying a plan selected from the group consisting of an examination plan for the patient and a therapy plan for the patient determined for a specific medical problem using said data sets.

13. A method as claimed in claim 1 comprising generating said overview image by magnetic resonance tomography.

* * * * *